United States Patent [19]

Sahasrabudhe

[11] Patent Number: 5,705,351
[45] Date of Patent: *Jan. 6, 1998

[54] DIAGNOSIS OF CANCER USING TUMOR-MIMETIC CELL SURFACE ANTIGEN FROM CHEMICALLY MODIFIED NORMAL CELLS

[76] Inventor: Madhao B. Sahasrabudhe, 41 Saras Baug, Sion-Trombay Road, Deonar, Bombay 400088, India

[ * ] Notice: The term of this patent shall not extend beyond the expiration date of Pat. No. 5,635,361.

[21] Appl. No.: 806,766

[22] Filed: Feb. 26, 1997

Related U.S. Application Data

[63] Continuation-in-part of Ser. No. 328,668, Oct. 25, 1994, Pat. No. 5,635,361.

[51] Int. Cl.$^6$ .................. G01N 33/574; G01N 33/53
[52] U.S. Cl. .................. 435/7.23; 435/7.24; 435/7.1; 435/7.2; 435/961; 436/63; 436/64; 436/813
[58] Field of Search .................. 435/7.23, 7.24, 435/7.1, 7.2, 961; 436/63, 64, 813

[56] References Cited

U.S. PATENT DOCUMENTS

| | | | |
|---|---|---|---|
| 3,663,684 | 5/1972 | Freedman et al. | 424/1 |
| 4,132,776 | 1/1979 | Jeter | 424/101 |
| 4,211,766 | 7/1980 | Bjorklund | 424/88 |
| 5,030,621 | 7/1991 | Bystryn | 514/21 |
| 5,290,551 | 3/1994 | Berd | 424/88 |
| 5,635,361 | 6/1997 | Sahasrabudhe | 435/7.23 |

OTHER PUBLICATIONS

Iyer et al., "A Model Study for Determining the Mechanism of Exposure of Leukemia-specific Antigen on Dinitrophenylated Leukocytes", Indian Journal of Biochemistry & Biophysics (1979) 16:110–114.

Karande et al., "Isolation of Leukemia Specific Antigenic Macromolecular Moiety from Dinitrophenylated Normal Human Leukocytes", Proc. Indian Acad. Sci., (1978) vol. 87B(1):1–8.

Mehrishi et al., "Positively Charged Amino Groups on the Surface of Normal and Cancer Cells", Europ. J. Cancer (1970) 6:127–137.

Prema et al., "Immunological Cross–Reactivity of Antisera Raised with Fluro Diniro Benzyne Tagged Normal Human Leukocytes Against Human Leukaemic Cells", Ind. J. Cancer (1978) 15:53–57.

Prema et al., "Electrophoretic Mobility of (a) Normal Human Leukocytes, (b) Flurodinitrobenzene Tagged Normal Human Leukocytes and (c) Leukaemic Cells", Inc. J. Cancer (1977) 14:200–205.

Sahasrabudhe, et al., "Two–Fold Strategy in Cancer Research for Achieving (a) Lasting Cures from Cancer by Reversal of Malignant Cells of Normality and (b) Securing Immediate Interim Reliefs for Patents", Ind. J. Cancer (1968) 5:217–228.

Sahasrabudhe, "Role Immunology in the Management of Leukemia", Aspects of Allergy and Applied Immunology (1973) 6:16–29.

Sahasrabudhe et al., "Some Observations on the Use of Chemically Labeled Normal White Blood Cells as Antigens in Active Immunization of Leukaemia", Biomedicine (1974) 20:31–39.

Sahasrabudhe et al., "Studies on the Use of Chemically Tagged Normal White Blood Cells as Antigens for producing Specific Immune Response Against Human Leukemic Cells", The Indian Journal of Cancer (1972) 9(2):101–111.

Sahasrabudhe et al., "Development of a Specific Anti–Leukaemic Serum for the Treatment of Leukaemia in Clinics", Nature (1971) 232:197–198.

Sahasrabudhe et al., "Induction of Specific Autoimmune Response to Leukaemic Cells in Human Leukaemia Patient by chemically Tagged Normal 'O' Group White Blood Cells", Nature (1971) 232:198–199.

Sahasrabudhe et al., "Modification of Cell Surface Receptors/Antigens by In Situ Hydrophilic–Hydrophobic Interconversions, with Special Reference to Exposure of Tumor Specific Antigens on Normal Cell Surfaces", Biology of the Cancer Cell, Proceedings of the Fifth Meeting of the European Association for Cancer Research, Vienna 9–12 Sept. 1979, pp. 241–252.

*Primary Examiner*—Toni R. Scheiner
*Attorney, Agent, or Firm*—Morrison & Foerster LLP

[57] ABSTRACT

A tumor-mimetic cell surface antigen (TMCSA) is produced by chemical treatment of normal human cells with a nucleophilic reagent which causes a hydrophobic-hydrophilic interconversion at the cell surface, such as a halobenzene derivative or a benzene sulfonate derivative. This TMCSA cross-reacts with tumor antigens from every type of tumor examined of any histopathologic type. Cancer is detected by detecting the presence of lymphocytes sensitized to tumor antigens based on their reactivity with TMCSA in a binding assay or lymphocyte stimulation or migration inhibition assay.

20 Claims, 1 Drawing Sheet

FIG. 1

DIAGNOSIS OF CANCER USING TUMOR-MIMETIC CELL SURFACE ANTIGEN FROM CHEMICALLY MODIFIED NORMAL CELLS

CROSS-REFERENCE TO RELATED APPLICATIONS

This application is a continuation-in-part of U.S. Ser. No. 08/328,668 filed 25 Oct. 1994, which issued as U.S. Pat. No. 5,635,361 on the date of Jun. 3, 1997.

BACKGROUND OF THE INVENTION

1. Field of the Invention

The invention in the fields of immunology and medicine relates to methods for early detection of cancer using in vitro assays. The disclosed methods detect in a person with cancer the presence of lymphocytes sensitized to weak tumor antigens. These are revealed by measuring reactivity with a unique tumor-mimetic cell surface antigen which appears to be cross-reactive among every type of cancer tested.

2. Description of the Background Art

Various forms of cancer may be treated and cured if detected sufficiently early in the disease process. Current diagnostic methods generally detect the presence of cancer only when the tumor load is greater than about $10^6$ cells. In many cases, detection at this stage already precludes successful treatment.

One approach to tumor diagnosis utilizes immunodiagnostic tools. The basis for immunodiagnosis is the existence on tumor cells of "tumor antigens," structures which are either absent from normal cells or expressed on tumor cells in a way which distinguishes them from normal cells. "Tumor-specific antigens" are true tumor antigens which occur only on neoplastic cells but not on normal cells at any stage of development. "Tumor-associated" antigens occur on tumor cells and on some normal cells under conditions in which the individual does not become tolerant and can theoretically respond to the tumor. Tumor-associated antigens can be considered abnormally expressed antigens of normal tissues and are commonly either "oncofetal" antigens or differentiation antigens. Oncofetal antigens are antigens normally expressed during embryogenesis but absent (or present at very low levels) on normal adult cells. They reappear in tumor cells or during tumor growth. Differentiation antigens are expressed in some adult tissues but not others; they reappear inappropriately in certain tumors.

Tumor antigens demonstrate varying degrees of expression across tumor types. Tumor-specific antigens of chemically-induced tumors are usually unique to the particular tumor. Antigens on virally-induced tumors are typically shared on tumors caused by the same virus. Tumor-associated antigens are commonly more cross-reactive. For example, certain antigens are found on many tumors of one histologic type, such as leukemias or adenocarcinomas or sarcomas. However, to date, there have been no reports of an antigen or antigens common to all tumors and absent from normal tissues. The existence of tumor antigens serves not only as the basis for approaches to immunotherapy of cancer, but also provides the foundation for immunodiagnosis of cancer. For reviews of tumor antigens and immunodiagnosis of cancer, see, for example, Herberman, R. B., *Am. J. Clin. Pathol.* 68 (5 Suppl):688–698 (1977); Sulitzeanu, D., *Adv. Cancer Res.* 44:1–42 (1985); Fair W. R., *Prog. Clin. Biol. Res.* 269:289–311 (1988); Goldenberg D. M., *Am. J. Med.* 94:297–312 (1993).

A well-known oncofetal antigen is carcinoembryonic antigen (CEA) (for example, U.S. Pat. No. 3,663,684) which is a glycoprotein shared between human colon cancer cells and normal cells of fetal gut, pancreas and liver. The presence of circulating CEA, presumably shed from colon cancer cells, allows the use of anti-CEA antibodies to detect tumors or monitor patients undergoing any type of tumor therapy.

Typically, antibodies specific for antigens that are unique to tumor cells, or prevalent on tumor cells in comparison to normal cells, serve as the basis for immunodetection of tumors. Sensitized lymphocytes, mainly T lymphocytes, which are specific for tumor antigens, can be detected by their reactivity to antigens against which they have been sensitized. Study of such cells in the tumor-host context have been largely aimed at isolating, enriching and activating these T cells, in vitro or in vivo, as effectors of tumor-specific immunotherapy. Tumor antigens have to be presented in association with MHC (major histocompatibility complex) proteins both for activating the immune system via T cells and also for the generation of effector T lymphocytes which recognize MHC-associated-antigens on cancer cell surfaces and kill these cells by cytolytic mechanisms. Even when the cancer cells do not possess tumor antigens in association with MHC, immune surveillance may become activated in an indirect fashion. Thus, when cancer cells disintegrate as a result of apoptosis, tumor antigens released into the circulation can be taken up and processed by host macrophages and other types of antigen-presenting cells and then presented in proper association with MHC glycoproteins to T lymphocytes resulting in the activation and release of primed or activated T (and B) lymphocytes into circulation. This indirect path for priming T and B lymphocytes, following natural apoptosis of early cancer cells, provides an opportunity for cancer cells to establish a firm foothold in the host and gain a head-start before the host immune system is fully activated and operational toward them. This explains the presence of activated T and B lymphocytes in the host, even when cancer cells do not display their tumor antigens in association with MHC products. Direct evidence for activated B lymphocytes comes from the detection of circulating tumor specific antibodies in tumor-bearing subjects.

It is one goal of the present invention to detect the presence of very small numbers of primed T lymphocytes in circulation in cancer patients. Even when primed T lymphocytes are present in circulation, cytolysis of cancer cells by conventional tumor-specific cytotoxic T lymphocytes (CTL) will not occur unless the tumor antigens are presented in proper association with MHC on the cancer cell surface. An activated host immune system cannot exert its effector function, in the form of cytolysis by CTL of cancer cells because of the hypothetical absence of obligatory presentation of "non-self" antigens in association with MHC on cancer cell surfaces. Direct demonstration of presence (or absence) of MHC on cancer cell surfaces has been attempted using immunohistochemistry. Ruiz-Cabello et al., *Adv. Expt. Med Biol* 233:119–128 (1988) examined tumor specimens from 9 different types of cancers. Except for few sarcomas, where MHC class I antigens were undetectable, none of the other cancers showed complete absence. In light of the circumstantial evidence pointing to virtual absence of functional MHC products on cancer cell surfaces, the immunohistochemical data cited above may mean that MHC molecules, if at all present, may be in a form which prevents recognition by a immunohistochemical reagent.

The present inventor and his colleagues discovered the existence of immunological "cross-reactivity" between human leukemia cells and normal leucocytes which had been modified or "tagged" with the chemical agent 1-fluorodinitrobenzene (FDNB). This previous work is described in more detail below and in the following references, which are hereby incorporated by reference in their entirety: Iyer, P. K. et al., *Indian J. Biochem. Biophys.* 16:110–114 (1979); Karande, A. A. et al., *Proc. Indian Acad. Sci.* 87B:1–8 (1978); Prema, S. et al., *Ind. J. Cancer* 15:53–57 (1978); Prema, S. et al., *Ind. J. Cancer* 14:200–205 (1977); Sahasrabudhe, M. B. et al., *Biomedicine* 20:31–39 (1974); Sahasrabudhe, M. B. et al., *Ind. J. Cancer* 9:101–111 (1972); Sahasrabudhe M. B. et al., *Nature* 232:198–199 (1971); Sahasrabudhe M. B. et al., *Nature* 232:197–198 (1971). This work was further reviewed in Sahasrabudhe, M. B., In: *Biology of the Cancer Cell*, Proc. 5th Meeting Europ. Assoc. Canc. Res., 1979, pp. 241–252.

The basis for the present inventor's discoveries, both past and disclosed herein, lies in the fact that hydrophilic groups in cell membranes are exposed at the cell surface and are in contact with the surrounding aqueous environment, whereas hydrophobic groups are sequestered away from the aqueous phase and generally buried in the membrane (Singer, S. J., In: *STRUCTURE AND FUNCTION OF BIOLOGICAL MEMBRANES*, L. I. Rothfield, ed., pp. 145–222 (1971); Singer, S. J., *Ann. Rev. Biochem.* 43:805–833 (1974); Nicolson, G. L. *Int. Rev. Cytol.* 3989–90 (1974)). The maintenance of hydrophobic groups on the outer cell surface requires the expenditure of energy and is destabilizing. The surface of a normal human lymphocyte contains about $9 \times 10^5$ amino groups (Mehrishi, J. N. et al., *Europ. J. Cancer* 6:127–137 (1970)). Progressive in situ blocking of these positively charged groups by chemical manipulation results in increasing cell surface negativity (Sahasrabudhe, M. B. *Indian J. Cancer* 5:217–228 (1968); Prema, S. et al., *Indian J. Cancer* 14:200–205 (1977).

1-fluoro-2,4-dinitrobenzene (fluorodinitrobenzene or FDNB) is a highly reactive compound which combines with amino groups (Sanger, F., *Biochem J.* 45:563–574 (1949) at physiological pH and temperature (Eisen, H. N. et al., *J. Amer. Chem. Soc.* 75:4583–4585 (1953), forming a fairly stable complex. As more surface amino groups are complexed with FDNB, cell surface negativity increases until all exposed amino groups are blocked. Beyond this point there should neither be an increase nor decrease in cell surface negativity unless other alterations occur in the membrane topography.

The present inventor and his colleagues found changes in the electrophoretic mobility (Ambrose, E. J. *Cell Electrophoresis* J. A. Churchill, London, 1965) of human leucocytes modified with very low concentrations of FDNB (Sahasrabudhe, 1968, supra; Prema et al., 1977, supra). Cell surface negativity increased until FDNB modification reached about $10^4$ molecules per cell, above which point surface negativity diminished. This was interpreted as indicating the appearance of new positively charged sites and/or disappearance of pre-existing negatively charged sites from the exposed cell surfaces. The maximum surface negativity attained by FDNB-tagged normal cells was in the same range as the surface negativity of "unmodified" leukemia cells.

Immunological techniques were used to examine the cell surface for appearance of new antigens or loss of existing antigens after FDNB modification. Antibodies were raised in rabbits against various FDNB-modified cell preparations (Sahasrabudhe, M. B. et al. *Ind. J. Cancer* 9:101–111 (1972); Prema, S. et al., *Indian J. Cancer* 15:53–57 (1978)). The antisera did not react with normal leucocytes but showed significant agglutination of leukemia cells, indicating the appearance on FDNB-modified cells of antigenic determinants which behaved as leukemia-specific antigens. Anti-leukemia antibodies were induced optimally using normal leucocytes modified to contain about $10^4$ molecules of FDNB per cell. The immune reactivity and cell surface negativity were found to be parallel, suggesting that optimum conformational changes were essential for exposing leukemia-specific antigenicity on FDNB-tagged cells.

The above antisera were subjected to absorption with pooled red blood cells (RBCs) and white blood cells (WBCs) from normal humans, which removed any species-related and HLA-related reactivity from the sera. Such absorbed sera reacted by agglutination and cytolysis with multiple types of leukemia cells (Sahasrabudhe et al., 1971, supra) including myeloid and lymphoid leukemias, suggesting that FDNB treatment induced a common leukemia antigen.

The present inventor and his colleagues discovered the presence in leukemia patients of cell-mediated immunity which was manifest as reactivity against FDNB-modified cells by leucocyte migration inhibition techniques, indicating the presence of immune reactivity toward leukemia-associated antigens. This was further supported by immunotherapeutic efficacy of FDNB-tagged cells in leukemia patients (Sahasrabudhe, M. B. In: *Aspects of Allergy and Applied Immunology* 6:16–29 (1973); Sahasrabudhe, M. B. et al., *Biomedicine* 20:31–39 (1974)).

The acquired leukemia-associated antigenicity of FDNB-treated (also termed "dinitrophenylated") leucocytes was not simply due to the presence of the dinitrophenyl (DNP) moiety, as anti-DNP sera did not react with FDNB-tagged cells (Karande & Sahasrabudhe, 1978). That the DNP moiety could be found in the membrane was shown using $^{14}$C-labeled FDNB to modify the cells. However, the DNP was not in a form accessible to antibodies, indicating that it was most likely internalized. Dinitrophenylation of an isolated protein, bovine serum albumin (BSA), using a maximum of ten molecules of FDNB per molecule of BSA, increased the hydrophobicity of BSA monolayers (Iyer, P. K. et al., *Indian J. Biochem. Biophys.* 16:110–114 (1979)). The conformational changes caused by FDNB tagging were transient and were reversed upon incubation in the absence of FDNB by about 48 hours. Examination of the effect of dinitrophenylation on expression of HLA antigens on normal human lymphocytes demonstrated the complete disappearance of some HLA antigenic determinants or acquisition of new HLA reactivities not formerly present, as might be expected with such perturbation of the membrane (Desai, K. R. *Studies on human leucocyte antigens*, M.Sc. Thesis, University of Bombay (1973).

Studies were performed to isolate the newly exposed leukemia-associated antigens from FDNB-tagged leucocytes using affinity chromatography with purified antibodies specific for FDNB-treated cells (Karande, A. A. et al., *Proc. Indian Acad. Sci.* 87B: 1–8 (1978)). Two macromolecular moieties with molecular weights of about 21 kDa and 48 kDa were isolated. These purified antigens could immunize animals to produce antibodies specifically reactive with leukemia cells and FDNB-modified normal human leucocytes, but not with unmodified normal cells.

The present inventor's interpretation of the foregoing observations was as follows: Conversion of $10^4$ hydrophilic amino groups on cell surfaces into dinitrophenylated hydrophobic groups constitutes a sufficiently major change to induce considerable perturbation in cell surface topography. This would result in the exposure of new surface antigenic sites on leucocytes which resembled or mimicked the surfaces of leukemic cells. Furthermore, FDNB-treated normal cells exhibited increased membrane fluidity characteristics more typical of leukemia cells than normal cells. Thus, hydrophilic-hydrophobic conversions at the cell surface can expose cryptic structures or antigens. Because controlled hydrophilic-hydrophobic interconversions induced a leukemia-associated antigen on the surface of a normal leucocytes, such antigens would not be a direct gene product of a leukemic cell arising from mutation preceding malignant transformation. Rather, such antigens may exist in cryptic forms in normal leucocyte membranes and undergo expression during the process of oncogenic transformation.

A number of references listed below are directed to antigens associated with tumors in human, although none disclose any tumor antigen, let alone highly cross-reactive tumor antigens, produced in normal cells by chemical treatment as disclosed by the present inventor herein and in prior publications. These include U.S. Pat. Nos. 3,663,684, 4,132, 776, 5,030,621, 5,194,384, 4,211,766. U.S. Pat. No. 5,290, 551 discloses haptenized tumor vaccines wherein tumor cells are modified with the haptens DNP, TNP or AED to increase their immunogenicity as cells or as cell extracts containing haptenated tumor antigens. The host is first immunized to the particular hapten before being treated with such a vaccine. No mention is made of hapten-modified normal cells mimicking tumor antigens.

In general, degradation products or shed antigens from tumor cells would not be detectable before the tumor achieves a mass of above about $10^6$ cells (or a size of 400 µm diameter). Furthermore, tumor degradation products entering the circulation would be uniformly distributed and diluted in about 7 liters of blood volume, making detection quite difficult. According to the present invention, detection of lymphocytes sensitized to tumor antigens using a "universal" tumor-mimetic cell surface antigen (TMCSA) will allow earlier detection of a broad array of cancer types at stages which currently go undetected.

As currently practiced, in vitro assays of lymphocyte activation or stimulation entail the measurement of cell growth (i.e., proliferation) by incorporation of radioactive precursors of DNA, most typically $^3$H-thymidine or $^{125}$I-iododeoxyuridine, into proliferating cells. Such assays, while sensitive, usually require 3–7 days. An assay detecting a sensitized lymphocyte which can be carried out in a shorter time frame would contribute to present diagnostic capabilities. An assay which is rapid, simple, requires little blood per sample and avoids the use of radioisotopes would be of great utility. While colorimetric assays to detect or enumerate cells based on measuring enzymatic activity are known in the art (Landegren, U., *J. Immunol. Meth.* 67:379–388 (1984); Mosmann, T., *J. Immunol. Meth.* 65:55–63 (1983); Neumann, H., et al., *Proc. Natl. Acad. Sci. USA* 73:1432 (1976); Culvenor, J. G., et al., *J. Immunol.* 126:1974 (1981); Hashimoto, N. et al., *J. Immunol. Meth.* 90:97–103 (1986); EPO publication 0122028 (17 Oct. 1984)), none of the above are designed to detect an antigen capable of being bound by the cells and which is conjugated to an enzyme acting as a detectable label.

Thus, the prior art lacks assays which can detect any type of cancer using a single antigen preparation. Furthermore, there is a deficiency in the art in detecting such a sensitized "tumor-cognitive" state using assays which may take only a few hours, as well as more traditional in vitro lymphocyte stimulation assays. The methods of the present invention are addressed to all of these deficiencies.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention is based on the discovery that TMCSAs are exposed or exteriorized on the surfaces of normal cells by controlled in situ hydrophilic-hydrophobic interconversion. This is accomplished using nucleophilic reagents such as fluorodinitrobenzene (FDNB) and related compounds. As described herein, such TMCSAs are about 200- to 500-fold more potent in the ability to reveal the presence of sensitized lymphocytes (by in vitro assays) than are antigens obtained from the surfaces of tumor cells.

The present invention is thus directed to a method for detecting the presence of a non-leukemia form of cancer in a subject having lymphocytes sensitized to a tumor antigen, which method comprises (a) obtaining a sample of blood from the subject; and (b) assaying the reactivity of leucocytes of the sample in vitro with a tumor-mimetic cell surface antigen (TMCSA) which TMCSA is produced by treating cells with a chemical agent which is a nucleophilic reagent with one leaving group and between one and three electron-withdrawing groups having one or more of the following properties when the cells are treated at a temperature and pH which are non-toxic:

(i) converts hydrophilic sites to hydrophobic sites on the surface of the cells;

(ii) causes a gain or loss of HLA antigens on the surface of the cells; or (iii) causes a change to the surface of leukocytes similar to changes induced by fluorodinitrobenzene under substantially similar conditions wherein the TMCSA is in the form of either:

(A) intact normal human cells which have been chemically treated with the chemical agent such that TMCSA is present on their surface;

(B) solubilized membranes of the treated cells of (A); or (C) affinity purified TMCSA produced from the solubilized membranes of (B) using a TMCSA-specific antibody, wherein the detection of reactivity with the TMCSA indicates the presence of the non-leukemia form of cancer in the subject.

In this method, the chemical agent is preferably a halobenzene derivative or a benzene sulfonate derivative. The treated normal human cells are preferably leucocytes or skin cells.

The assay in the above method may comprise measuring the binding of the sample leucocytes to the TMCSA, preferably affinity purified TMCSA. The binding is preferably measured in an enzyme immunoassay using enzyme-labeled TMCSA wherein a preferred enzyme label is horseradish peroxidase.

In another embodiment, the above assay measures the stimulation or activation of leucocytes in the sample by the TMCSA, for example, the proliferation of lymphocytes, the inhibition of migration of the sample leucocytes stimulated by the TMCSA, or the production of a cytokine by the sample leucocytes.

In the foregoing methods, the type of cancer may be an adenocarcinoma, a squamous cell carcinoma, a breast duct cell carcinoma, a sarcoma, a melanoma, a hemangioma, a hepatoma or a lymphoma.

The present invention is further directed to a method for detecting the presence of lymphocytes in a subject which are sensitized to a tumor antigen and are reactive with TMCSA, which method comprises (a) obtaining a sample of blood from the subject;

(b) assaying in vitro (I) reactivity other than antibody secretion, or (ii) the binding, of leucocytes of the sample with a TMCSA produced by treating cells with a chemical agent which is a nucleophilic reagent with one leaving group and between one and three electron-withdrawing groups; having one or more of the following properties when the cells are treated at a temperature and pH which are non-toxic: (A) converts hydrophilic sites to hydrophobic sites on the surface of the cells; (B) causes a gain or loss of HLA on the surface of the cells; or (C) causes a change to the surface of leukocytes similar to changes induced by fluorodinitrobenzene under substantially similar conditions, which TMCSA is in the form of either:

(1) normal human cells which have been chemically treated with the chemical agent such that TMCSA is present on their surface;

(2) solubilized membranes of the chemically treated cells; or (3) affinity purified TMCSA produced from the solubilized membranes using a TMCSA-specific antibody, wherein detection of reactivity or binding of the leucocytes with the TMCSA indicates the presence of the sensitized lymphocytes.

Also provided is a method for monitoring therapy in a non-leukemia cancer patient to detect a therapeutic effect, which method comprises:

(a) subjecting the patient to a cancer therapy;

(b) obtaining a sample of blood from the patient at two or more time points during the therapy, after the therapy, or both;

(c) assaying in vitro (i) reactivity other than antibody secretion, or (ii) binding of leucocytes of the sample with a TMCSA produced by treating cells with a chemical agent which is a nucleophilic reagent with one leaving group and between one and three electron-withdrawing groups; having one or more of the following properties when the cells are treated at a temperature and pH which are non-toxic:

(A) converts hydrophilic sites to hydrophobic sites on the surface of the cells;

(B) causes a gain or loss of HLA on the surface of the cells; or (C) causes a change to the surface of leukocytes similar to changes induced by fluorodinitrobenzene under substantially similar conditions which TMCSA is in the form of either:

(1) normal human cells which have been chemically treated with the chemical agent such that TMCSA is present on their surface;

(2) solubilized membranes of the chemically treated cells; or (3) affinity purified TMC SA produced from the solubilized membranes using a TMCSA-specific antibody, wherein a decrease in the reactivity or binding from one time point before, during or after therapy to a subsequent time point during or after therapy is an indication of a therapeutic effect.

In the foregoing methods, the chemical agent is preferably a halobenzene derivative or a benzene sulfonate derivative.

The invention also includes a kit for use in an enzyme assay to detect the presence of lymphocytes sensitized to a tumor antigen, the kit being compartmentalized to receive in close confinement therein one or more containers, the kit comprising a first container containing a TMCSA preparation conjugated to an enzyme, which TMCSA comprises (a) normal human cells which have been chemically treated with chemical agent which is a nucleophilic reagent with one leaving group and between one and three electron-withdrawing groups having one or more of the following properties when the cells are treated at a temperature and pH which are non-toxic:

(i) converts hydrophilic sites to hydrophobic sites on the surface of the cells;

(ii) causes a gain or loss of HLA antigens on the surface of the cells; or (iii) causes a change to the surface of leukocytes similar to changes induced by fluorodinitrobenzene under substantially similar conditions (b) solubilized membranes of the chemically treated cells; or (c) affinity purified TMCSA produced from the solubilized membranes using an TMCSA-specific antibody, which preparation binds detectably to lymphocytes sensitized to a tumor antigen.

The kit may further comprise a container containing a chromogenic substrate for the enzyme and optionally, a plurality of additional containers containing reagents needed for the assay. In the foregoing kit, the chemical agent with which the cells have been treated is preferably is a halobenzene derivative or a benzene sulfonate derivative.

DESCRIPTION OF THE PREFERRED EMBODIMENTS

Hydrophilic groups at the cell surface normally remain in contact with the surrounding aqueous medium, whereas hydrophobic groups sequester themselves in hydrophobic environment away from the extracellular milieu. Conversion of cell surface hydrophilic groups into hydrophobic groups by chemical manipulation renders the cell surface unstable. The present inventor has discovered that hydrophilic-hydrophobic interconversions cause conformational changes leading to the exposure on normal cell surfaces of new markers or antigenic sites. In particular, by using fluorodinitrobenzene (FDNB) to chemically transform about $10^4$ hydrophilic sites/cell on normal human leucocytes into hydrophobic sites, the present inventor has discovered the generation of an antigen or marker that is present on every type of tumor cell tested. While these antigens were originally thought to be shared only with leukemia cells, the inventor has now discovered that these antigens, termed "tumor-mimetic cell surface antigens" or "TMCSA," are present on every type of tumor cell.

The present invention is directed to a method for early detection of cancer in a subject by measuring the reactivity of lymphocytes which have been sensitized by tumor antigen, but such antigens are too weak to reveal the existence of these sensitized lymphocytes in a laboratory assay. Due to its unique strength, the TMCSA of the present invention stimulates such cells and allows their detection, indicating the presence of cancer, even when the number of tumor cells are exceedingly low. These sensitized lymphocytes are preferably obtained from the blood of the subject being tested. However, they can be obtained from any other tissue source known to contain lymphocytes, for example, lymph or lymphatic tissues.

The above method utilizes any known assay capable of measuring the reactivity of sensitized lymphocytes to an antigen, including but not limited to, lymphocyte proliferation, lymphocyte or leucocyte migration inhibition, lymphocyte mediated cytotoxicity, etc. A preferred assay is an enzyme-linked assay developed by the present inventor, which measures in vitro binding of enzyme-conjugated TMCSA to the sensitized lymphocytes. Other labels may also be used, for example, fluorescence-based assays, by substituting another type of detectable label for the enzyme label.

Antibodies specific for the TMCSA are used as part of the present invention, in that they permit affinity purification of TMCSA for use in the in vitro assays. Furthermore, such antibodies have additional utilities in methods for early detection of cancer in vivo. In such methods, labeled antibodies are used to detect foci of tumor cells in vivo and serve to localize the tumor using immunoscintigraphic or radioimmunodetection methods.

The simplicity and economy of the present assay creates the possibility of routinely screening apparently healthy people, for example, every six months, to identify those with incipient cancer using a relatively simple and inexpensive assay. Such screening is even more important for people with risk factors (e.g., genetic or behavioral) for cancer development. Detection of lymphocytes reactive to TMCSA would serve as an indicator of the presence of a tumor long before such a tumor is detectable radiologically or clinically. This detection would offer the possibility of early surgical or medical intervention and increase the probability of cure. The methods of the present invention can detect persons having low numbers of tumor cells, as few as $10^3$. As long as tumor cells are at a site where they are accessible to cells of the immune system (and can sensitize lymphocytes), the presence of lymphocytes sensitized to tumor antigens can be detected by the methods of the present invention.

The present methods have improved diagnostic value relative to biopsy, as confirmed by subsequent direct surgical exploration of subjects who tested positive using FDNB-tagged cells or TMCSA as reagents. Biopsies can give false negative results if not obtained from the correct area.

TMCSA

Figure 1:
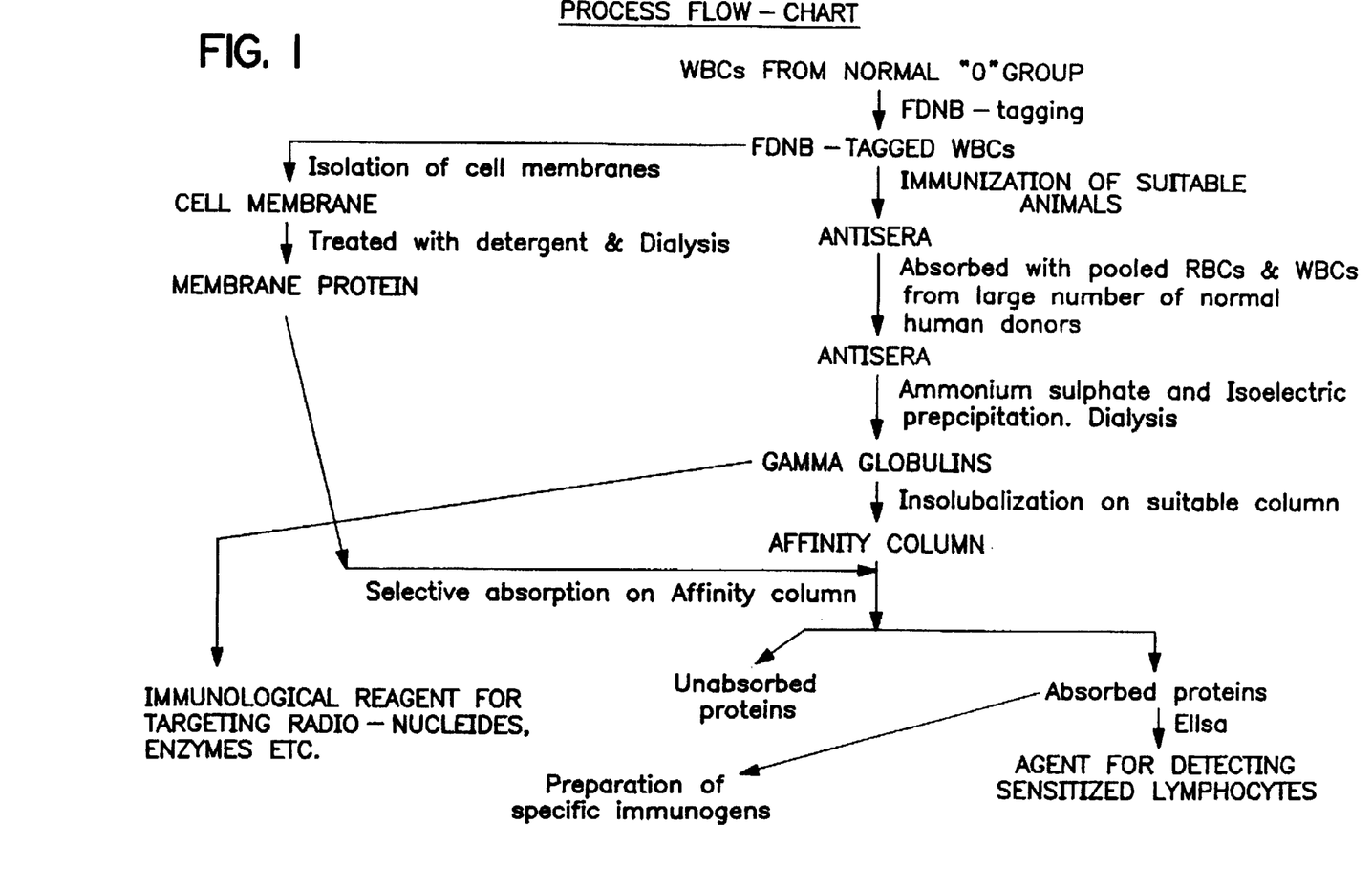
FIG. 1 illustrates schematically the preparation and uses of TMCSA.

A schematic illustration describing the preparation and uses of TMCSA is shown in FIG. 1.

TMCSA is preferably induced by treating cells with FDNB and its closely related congeners, dinitrochlorobenzene (DNCB) or trinitrochlorobenzene (TNCB, also known as picryl chloride).

For a chemical agent to be useful in generating TMCSA of the present invention, the agent would have similar chemical/physical properties to FDNB as described below. Functionally, the agent is one which (a) converts hydrophilic sites to hydrophobic sites on the surface of cells at a temperature (preferably room temperature) and at a pH non-toxic to cells and/or (b) causes a gain or loss of HLA antigenicity on the surface of the cells the above nont-toxic temperature and pH. Cells treated with such an agent to induce TMCSA are referred to herein as "chemically-treated" or "treated" or "chemically modified" or "tagged" cells. More, typically, below, they will be described as "FDNB-treated" or "FDNB-tagged" cells. While FDNB represents a preferred embodiment, it is not intended to limit the invention to TMCSA generated by treating cells with FDNB; other useful agents having similar properties are discussed below.

J. Klein, Immunology. *The Science of Self-Nonself Discrimination*, John Wiley & Sons, New York, 1982, pages 358, 359, 469 (incorporated by reference) summarizes various aspects of dinitrophenyl and trinitrophenyl haptens, and their reactive donor compounds as used in immunology. Various halide-substituted nitrophenyls (both dinitro- and trinitrophenyl) bind to proteins by interacting with $\epsilon$-amino groups of lysine residues (and the N-terminal amino group) (Klein, supra, page 359 first paragraph). Different reactive forms of these compounds such as FDNB (designated "DNFB" by Klein), DNCB and picryl chloride (trinitrochlorobenzene or TNCB) are noted in Klein, supra, at page 359, first paragraph and FIG. 10.5 at page 358. Cell-mediated immune response in the form of contact sensitivity can be induced by chemical modification of cell surfaces, for example using TNCB, DNCB or DNFB (Klein, supra, at 469).

Thus, these three analogous compounds are functionally equivalent in their reactivity with free amino groups on proteins (by nucleophilic substitution reactions) when they are applied to cells in vitro or in vivo. For a discussion of the chemistry of the types of reactions needed for the generation of TMCSA, see, for example, Allinger, N. L. et al., *Organic Chemistry*, Worth Publishers, New York, 1971, pages 417–420 and 763–764 (which reference is hereby incorporated by reference in its entirety). The chemical agent must be one which produces a nucleophilic substitution at a carbon atom (or amino nitrogen) which is susceptible to nucleophilic attack. With benzene compounds, such as the various halogenated benzenes discussed above, nucleophilic substitution occurs when strong electron-withdrawing groups are ortho or para to the leaving group of the agent. The best leaving groups are those that give the most stable molecule or ion after they depart. In general, the less basic the leaving group, the more easily it departs from carbon. In addition to water and alcohols, halide ions are among the best leaving groups (rank order of I>Br>Cl>F), as are sulfonates, sulfates and carboxylates.

Such reactions occur with halobenzenes substituted at the ortho position with a single nitro group, or disubstituted at the ortho and para positions with two nitro groups, or trisubstituted at ther two ortho and the para positions with three nitro groups. The halogen substituent is the leaving group, whereas the nitro functions are the electron-withdrawing groups. As the number of nitro groups (or other electron withdrawing groups) on the benzene ring is increased, the reaction occurs more readily at lower temperatures, thereby not requiting exogenous heating. The mechanism operating in the nucleophilic substitution reactions of ortho- and para nitrobenzene compounds is bimolecular, involving formation of an intermediate (Meisenheimer complex) in which both the nucleophile and the leaving group are bonded to carbon. In addition to nucleophilic substitutions at unsaturated carbon, nucleophilic substitutions are well-known to take place at free amino groups, such as at the N-terminal amino group of a protein or peptide, or at $\epsilon$-amino groups of lysine residues. This is the basis of the Sanger method for determining the N-terminal amino acid of a protein and sequencing the protein by sequential reactions at its N-terminus.

As mentioned above, organic sulfonates (esters of alcohols and sulfur derivatives) and sulfates are used in nucleophilic substitution reactions because the ions are good leaving groups like the halide ions discussed above. Thus, nitro, dinitro or trinitro benzene sulfonates are useful as agents which induce TMCSA on the cell surface in the same way as nitrohalobenzenes as described. Preferred sulfonates are dinitrobenzene sulfonate (DNBS) and trinitrobenzene sulfonate (TNBS). DNBS and TNBS are known agents for introducing the dinitrophenyl moiety (as a hapten) onto proteins and have been used extensively in immunology and immunochemistry.

Other references which describe the chemical substitution of proteins, peptides and cells (as well as direct treatment of animals) by nucleophilic substitution reactions include Eisen, H. N. et al., *J. Amer. Chem. Soc.* 75:4583–4585 (1953); Eisen, H. N. et al., *J. Exp. Med* 110:187–206 (1959); Okuyama, T. et al., *J. Biochem.* 47:454–466 (1960); Satake, K. et al., *J. Biochem.* 47:654–660 (1960); Battisto, J. R. et al., *Nature* 212:156–157 (1966); Rittenberg, M. B. et al., *J. Immunol.* 97:421–430 (1966); Rittenberg, M. B. et al., *Proc. Soc. Exp. Biol. Med* 132:575–581 (1969); Phanuphak, P. et al., *J. Immunol.* 112:849–851 (1974); Claman, H. N., *J. Immunol.* 116:704–709 (1976), which references are hereby incorporated by reference in their entirety.

In general, any molecule of the type described above having the stated properties of nucleophilic substitution at a carbon or nitrogen on a molecule (preferably a protein) at the cell surface, and which has the requisite reactivity at a temperature and a pH tolerated by cells and which is not otherwise toxic to cells, is within the scope of this invention as an agent for inducing TMCSA. The skilled artisan will understand how to use any such compound in the context of the present invention in accordance with the description and exemplification provided below.

The TMCSA, for example, in the form of FDNB-modified cells is prepared by incubating equal volumes of a cell suspension, preferably a leucocyte suspension, having about $10^7$ cells/ml and 31 pg/ml FDNB in normal saline. (The FDNB solution is prepared by dissolving 31 mg FDNB in 100 ml normal saline as stock, with appropriate dilutions for use.) At this concentration, there are $10^{11}$ molecules/ml of FDNB. The cells are mixed and shaken for 10–15 min at room temperature. The pH is adjusted to 7.2–7.4 with $NaHCO_3$. The unreacted FDNB and HF formed are removed by repeated washing of the cells in large volumes of saline. These cell preparations, having theoretically $10^4$ molecule of FDNB/cell, are resuspended in sterile isotonic saline at a concentrations of $10^7$ cells/ml. The conditions for chemical modification of the cell surface by other agents described above are substantially equivalent to those described for FDNB with modifications in temperature, pH and reagent concentrations that would be evident to the skilled artisan.

Anti-TMCSA antibodies (see below) are used as affinity probes to purify the antigen(s) from extracts of treated cells. Such preparations have been shown to include a 21 kDa and a 47 kDa moiety. Such affinity-purified TMCSA is immunogenic and can induce antibodies reactive with any type of tumor cell (as well as with FDNB-treated normal cells). Affinity purified TMCSA is then used in the assay methods of the present invention to reveal tumor-sensitized lymphocytes. Furthermore, affinity-purified TMCSA can be used for production of improved polyclonal and monoclonal antibodies for reagent preparation or for in vivo diagnostic use.

The TMCSAs useful in the methods of the present invention are produced by inducing a hydrophilic-hydrophobic interconversion at the cell membrane. This is best accomplished using FDNB, but as detailed above, other chemical agents which cause similar changes in cells at room temperature or temperatures which cells can tolerate without lysis or other types of permanent damage, and which are reactive at non-toxic pH, may also be used. The TMCSA may be in the form of whole cells treated with the agent, preferably FDNB. In another embodiment, the TMCSA is in the form of subcellular membrane preparations made from such treated cells. In yet another embodiment, the TMCSA is in the form of antigens isolated from such treated cell membrane preparations using immunoaffinity chromatography with antibodies specific for TMCSA.

Besides sharing this common TMCSA with all the cancers studied, the chemically modified cells of the present invention show a loss of HLA antigens and show peculiar "capping" phenomena characteristic of cancer cells (Sahasrabudhe, 1980, supra). Study of the sequence of events taking place immediately upon tagging with FDNB (or other chemical agents), may offer useful leads for understanding certain steps in carcinogenesis and also offer a simple method for screening chemicals or biologicals for carcinogenicity. FDNB (as well as other halobenzene and sulfobenzene derivatives as well as non-aromatic sulfonates) are known carcinogens. FDNB added to normal cells in vitro first reacts with free-$NH_2$ groups of cell surface proteins, to form dinitrophenylated proteins which would be regarded as "foreign" and "non-self" by the immune system. An early consequence is the formation of a complex between this "non-self" protein and endogenous MHC molecules via the peptide-binding-groove of the MHC molecules. Hence, an MHC molecule, firmly anchored in the hydrophobic layers of cell membrane, takes on an appendage of an auxiliary protein with heavy hydrophobic chemical groups bound thereto. This newly formed appendage with heavy hydrophobic groups has a natural tendency to intercalate into the hydrophobic layers of the membrane and exert force on the extracellular domains of the MHC molecule towards the hydrophobic part of the membrane. The MHC molecule would have two hydrophobic regions (the transmembrane domain and the chemically modified hydrophobic sites) interacting with the hydrophobic membrane layers. Such changes induce stress and strain on the MHC molecule which could promote shearing at its weakest links. Such a break would express itself as the change in HLA antigen expression (as observed) and also as increased freedom of movement in the "loose" ends of the extracellular domains. The latter change has also been observed as capping of lectin binding sites for concanavalin A and wheat germ agglutinin (reviewed in Sahasrabudhe, 1980, supra)

RENDERING CANCER CELLS SUSCEPTIBLE TO IMMUNE SURVEILLANCE

Tumor cells per se, are inefficient in sensitizing host T and B lymphocytes, because tumor antigens are not presented in association with MHC. However, as discussed above, sensitization of T and B lymphocytes, through the presentation by host antigen-presenting cells of shed tumor antigens apparently does take place. The host is thus in a position to mount an immune attack on cancer cells. However, even if host effector cells are generated in this way, cancer cells may evade attack because their deficiency in MHC proteins prevents them from presenting antigens to lymphocytes in an immunologically recognizable form.

Two approaches may be taken to induce the expression of MHC-associated tumor antigens on cancer cells and bring them under immune surveillance. One approach comprises transfecting all the cancer cells in the body with MHC genes or other genes which regulated trafficking or surface expression of MHC gene products (such as TAP 1 and TAP 2 genes). However, successful transfection of MHC genes into 100% of cancer cells is highly unlikely. This approach is further complicated by the vast polymorphism of MHC genes in human populations. Although this approach is of theoretical interest, it appears impractical at this time. In contrast, in a preferred embodiment which takes advantage of the discovery of TMCSA by the present inventor, the cancer cells are passively coated with MHC-associated tumor antigens isolated from chemically-treated normal cells, for example cells treated with FDNB or other nucleophilic reagents as described herein.-This latter approach offers a much greater expectation of success than an MHC transfection approach. The present inventor has already isolated antibodies which bind specifically to tumor cells and leave normal cells, organs and tissues of the host intact. These antibodies are harnessed to carry and deliver the MHC-associated-tumor-antigens directly to cancer cells. To avoid "self neutralization" of the tumor antigens by the tumor-specific antibodies used in this method, a "sandwich" approach is employed. A first composition comprising tumor-reactive antibodies, for example rabbit antibodies specific for TMCSA induced as described below, is infused into a subject and permitted to bind to any available cancer cells. A second composition comprises anti-rabbit immunoglobulin antibodies (preferably made in another animal species) to which are bound MHC-associated-tumor-antigens. This second composition is administered and permitted to home to cancer cells by virtue of its specificity for the tumor-bound rabbit immunoglobulin (the first composition). Once delivered, the MHC-associated tumor antigens are now expressed on the previously deficient cancer cell. One skilled in the art will know how to test the effectiveness of this sandwich technology for selective delivery of MHC-associated-tumor-antigens to cancer cells by performance of routine vitro tests of antibody binding. Thus, one can easily measure binding of anti-tumor antibody (first composition) to cancer cells in vitro and binding of anti-Ig antibodies complexed with MHC-tumor antigens (second composition) to the cell-bound first antibodies, and thus to the cell surface.

PREPARATION OF ANTI-TMCSA ANTIBODIES

Polyclonal antibodies are produced in animals such as goats or rabbits by immunizing with a preparation of FDNB-modified normal cells. An example of a useful immunization regimen is as follows. Rabbits are immunized once a week for a standard period, generally about 12 weeks, by injections, preferably subcutaneous, of about $2 \times 10^7$ chemically treated (e.g., FDNB-tagged) cells. Ten days after the final injection, rabbits are bled. The serum is heat inactivated at 56° C. for 30 minutes.

Undesired antibodies reactive with various human antigens are removed by absorption with pooled RBC and pooled leucocytes from healthy donors using conventional methods. Immunoglobulin can then be precipitated at 50% ammonium sulfate saturation. The precipitate is dissolved in 0.15M phosphate buffered saline (PBS), pH 6.8 and dialyzed to remove the ammonium sulfate.

Experiments showing the reactivity of such sera with normal leucocytes and leukemia cells have been described in various references of the present inventor and his collaborators cited above. Polyclonal antibodies prepared in this way do not react with normal leucocytes (by agglutination) but showed significant reactivity with leukemia cells. These antibodies can be used to test for the presence of TMCSA, preferably on the surface of cells, in an unknown sample.

For producing a monoclonal antibody (mAb), any method which provides for the production of antibody molecules by continuous cell lines in culture may be used. As an immunogen, any TMCSA preparation, whether cellular, subcellular or affinity purified, may be used. These methods include, but are not limited to, the hybridoma technique originally described by Kohler and Milstein (1975, *Nature* 256:495–497). A hybridoma of rodent origin producing the mAbs of this invention may be cultivated in vitro or in vivo. For an overview of antibody production methods, see: Hartlow, E. et al., *Antibodies: A Laboratory Manual*, Cold Spring Harbor Laboratory Press, Cold Spring Harbor, N.Y., 1988.

Antibody molecules or fragments may be purified by known techniques, e.g., immunoabsorption or immunoaffinity chromatography, for example, using Staphylococcal protein A, or chromatographic methods such as HPLC (high performance liquid chromatography), or a combination thereof, etc. In a preferred method, the TMCSA mAb is purified from culture supernatant or ascites fluid.

The term "antibody" is also meant to include both intact molecules as well as fragments thereof which bind the antigen, such as, for example, $F(ab')_2$, Fab', Fab and Fv. It will be appreciated that these antigen-binding or epitope-binding fragments of the antibodies useful in the present invention may be used for the detection and quantitation of TMCSA as disclosed herein for intact antibody molecules. Such fragments are typically produced by proteolytic cleavage, using enzymes such as papain (to produce Fab fragments) or pepsin (to produce $F(ab')_2$ fragments) or by reducing the disulfide bridges.

The antibody, fragment or derivative useful in the present invention, may be prepared by using any of a number of techniques well-known in the art.

ASSAY METHODS

TMCSA Binding Assay

The present inventor has developed an in vitro method for detecting persons at risk of any type of cancers, based on the presence of sensitized lymphocytes which bind to TMCSA. Thus, the present of an incipient tumor results in the sensitization of lymphocytes in such a way that these cells react positively with a TMCSA preparation. A preferred way to measure such reactivity is by binding of TMCSA to lymphocytes.

An affinity purified TMCSA preparation is made by lysing DNFB-tagged cells, described above, and passing the lysate over an affinity column of anti-TMCSA antibody produced as described above. These methods are described in more detail in Karande, A. A. et al., *Proc. Indian Acad. Sci.* 87B:1–8 (1978).

Briefly, crude membrane preparations are made from FDNB-tagged cells by osmotic lysis. The material is centrifuged at 40,000×g and the pellet washed several times to remove soluble cytoplasmic material and nuclear material. These preparations are solubilized by incubating membranes with sodium dodecyl sulfate (SDS) at about 5.7 mg/3.6 mg protein for about 30 min at 37° C. Other concentrations and times well-known in the art may be used. See, for example, Neeman, Z., et al., Biochim. Biophys. Acta 266:255 (1972). The solubilized solution is centrifuged at 100,000×g for 1 hr to remove insoluble material. SDS is removed by prolonged dialysis against distilled water or by Sephadex gel filtration. Both these methods are well-known in the art. The membrane protein-containing preparation is suspended in 0.1M $NaHCO_3$, pH 8.5–9.0.

The anti-TMCSA immunoglobulin preparation, such as that described above, is coupled to CNBr-activated Sepharose beads using convention methods, by mixing and stirring overnight at 4° C. This material is subjected to extensive washing with PBS until the washings show spectrophotometric absorptions of less than 0.02 absorption units at 280 nm. The extent of coupling is generally about 90%; this can be estimated by determining the protein content of the washes. The antibody-Sepharose beads are stored at 4° C. in the presence of $NaN_3$.

The affinity chromatography may be performed as follows. The solubilized membrane preparation from DNFB-tagged cells (25–50 mg) is loaded onto an antibody-Sepharose column (20 g) equilibrated with 0.1M bicarbonate. The flow is stopped for about 10–15 minutes to allow antigen-antibody binding to occur. Unabsorbed material is washed with 40 ml of 0.1M bicarbonate. The absorbed material is eluted with 0.1M acetic acid (pH 2.5). For example, about 6 fractions each of 4 ml. may be collected. The eluate is neutralized with 2N NaOH and dialyzed against PBS, pH 6.8.

The preferred binding assay is an enzyme immunoassay (EIA) which may considered a modified ELISA. (For descriptions of EIA procedures in general, albeit directed to methods for antibody or antigen detection, see, Engvall et al., *Immunochem.* 8:871 (1971); Van Weeman et al., *FEBS Lett.* 15:232 (1971); Voller, A., *The Enzyme Linked Immunosorbent Assay* (ELISA), *Diagnostic Horizons* 2:1–7, 1978)) (Microbiological Associates Quarterly Publication, Walkersville, Md.); Voller, A. et al., *Bull. WHO* 53:55–65 (1976); Voller, A. et al., *J. Clin. Pathol.* 31:507–520 (1978); Butler, J. E., *Meth. Enzymol.* 73:482–523 (1981); or Maggio, E. (ed.), *Enzyme Immunoassay*, CRC Press, Boca Raton, Fla., 1980.)

The affinity purified TMCSA material described above conjugated to an enzyme label for use in this EIA. Horseradish peroxidase is a preferred enzyme. Other enzymes known to be useful in EIA may be used, including malate dehydrogenase, staphylococcal nuclease, Δ-5-steroid isomerase, yeast alcohol dehydrogenase, α-glycerophosphate dehydrogenase, triose phosphate isomerase, alkaline phosphatase, asparaginase, glucose oxidase, β-galactosidase, ribonuclease, urease, catalase, glucose-6-phosphate dehydrogenase, glucoamylase and acetylcholinesterase.

The method for conjugating the enzyme can be found in any standard immunoassay reference work. A preferred method employs glutaraldehyde.

The enzyme, when later exposed to its substrate, will react with the substrate in such a manner as to produce a chemical moiety which can be detected, for example, by spectrophotometric, fluorometric or by visual means. Typically, the substrate is a chromogenic molecule which yields a colored reaction product. Preferred substrates for peroxidase include amino antipyrine benzoic acid, tetramethylbenzidine (TMB), 2'2'-azino-di-(3-ethylbenzthiozoline) sulfonate (ABTS) or 3-amino-9-ethylcarbazol (AEC). Preferred substrates for other enzymes are well-known in the art.

Total peripheral blood leucocytes, mononuclear cells prepared by Ficoll-Hypaque gradient centrifugation, isolated lymphocytes, or T lymphocytes may be prepared from blood samples using conventional methods.

If the enzyme used has an endogenous enzyme counterpart, such as peroxidase, cells are first treated to block the endogenous enzyme activity. The cell preparation is incubated in a tube with the TMCSA-enzyme complex. The cells are subsequently washed by centrifugation several times until the supernatant has no remaining enzyme activity (tested using the chromogenic substrate). The cell pellet is then resuspended in a minimal volume, substrate for the enzyme is added, and the reaction allowed to proceed for the requisite time, which depends on the enzyme and the substrate. The amount of reaction product is assessed by measuring absorption at the appropriate wavelength for the colored reaction product. The amount of colored product is a reflection of the amount of TMCSA bound.

Controls in this assay include TMCSA-enzyme added to empty tubes (no cells), and, more importantly, leucocytes from healthy individuals (not harboring latent or premalignant lesions). Typically, such controls give readings of the order of 0.002 absorbance units. Sensitized lymphocytes from patients which have cancer of any histopathological type give values which are significantly higher, many in the are of about 0.200 absorbance units. Thus, sensitized lymphocytes have the capacity to bind the TMCSA. It is likely that B lymphocytes are the main cells detected in this assay.

Functional Lymphocyte Assays

The presence of TMCSA-specific sensitized T cells, indicating the presence of cancer, can be readily determined by testing the ability of the cells to be activated in the presence of the antigen. Many assays are available, and well known in the art, to measure early or late events in the T cell activation process. Example of such methods include, but are not limited to, T cell proliferation (which can be measured as the uptake of radiolabeled thymidine), the secretion of interleukin-2 or migration inhibition factors, intracellular calcium mobilization, translocation of particular membrane enzymes involved in inositol phosphate metabolism, and changes in expression of cell surface molecules (which can be determined by flow cytometry).

In one embodiment employing this method, peripheral blood lymphocytes of the test subject are removed and stimulated with the TMCSA. The TMCSA preparation is added to the lymphocyte cultures for several days. The time required for stimulation is a function of the proportion of sensitized cells in the blood sample, the activation state of these cells, and the potency of the stimulating preparation, and is readily determinable by one of skill in the art. After culture under such selective conditions, incorporation of radiolabeled thymidine is tested. In another embodiment, the culture supernatant is assayed for IL-2.

In a preferred embodiment, leucocyte migration inhibition is measured. Migration inhibition assays are known in the art (See, for example, Bloom, B. R. et al., eds., *IN VITRO METHODS IN CELL-MEDIATED AND TUMOR IMMUNITY*, Academic Press, N.Y., 1976, in particular, pages 607–676). A preferred lymphocyte migration inhibition assay is carried out as follows:

Ten ml of blood from a subject is collected over citrate or EDTA as anticoagulant. Immediately upon collection, 5 ml of 4% dextran is added to every 10 ml sample. RBCs are allowed to settle for about 1 hr. The supernatant fluid, along with buffy coat, was aspirated and centrifuged for 2 minutes at 1500 rpm to separate the white blood cells from the plasma, anticoagulant, etc. Leucocytes are freed from contaminating RBCs by osmotic shock treatment with 0.83% ammonium chloride for one minute.

The separated leucocytes which form a button at the bottom of centrifuge tube are resuspended in MEM medium supplemented with antibiotics and 10% fetal calf serum (FCS). The cells are centrifuged again at 1500 rpm for 2 min. This process of alternate washing and centrifugation is repeated several times, preferably four times, to free the cells from plasma and anticoagulants, etc. Washed cells are resuspended in fresh MEM (+antibiotics and FCS) to a concentration of about $10^8$ cells/ml. Viability of the cells is assessed by dye-exclusion. 75 µl of cell suspension is taken up in a capillary tube of approximately 0.5 mm inner diameter. One end of the tube is sealed, for example, with high vacuum silicon grease and plasticene.

Capillary tubes containing the cell suspension are centrifuged at 1500 rpm for 2 min to loosely pack the cells toward the sealed end of the tube. The capillary tubes are cut at the cell-medium interphase levels. Cut pieces containing cells are horizontally secured in migration chambers which preferably have an inner diameter 1.6 cm, depth of 2 mm, and capacity of 0.5 ml). The chambers are then filled with MEM. Control chambers are filled with MEM only, whereas the experimental chambers are filled with MEM containing TMCSA (100 µg protein per chamber). Individual chambers are covered with cover glass and sealed with high vacuum silicon grease. The assembly is incubated at 37° C. for 18 hr, allowing the cells to migrate out of the capillary tube.

The extent of migration of cells in the control and experimental chambers is monitored by determining the area traversed by the migrating cells. This can be accomplished in any of a number of ways known in the art. For example, a light is used to project the image of the migration area onto paper and the migration area traced. The are of this zone can then be calculated. Alternatively, the marked zone can be cut out and weighed; the weight is proportional to the migration area.

Sensitized lymphocytes recognize the specific antigen and respond in part by releasing cytokines which inhibit migration. Thus, in the presence of the specific antigen, migration is inhibited when sensitized lymphocytes are present in the cell suspension, whereas in controls lacking sensitized lymphocytes (or in the absence of antigen addition), migration is maximal.

THERAPY

The present inventor has conceived of the use of viable FDNB-tagged cells or products thereof for therapy of non-leukemia types of cancer. Therapeutic results in leukemia have already been reported and are cited above. As conceived herein, such preparations are used to treat individuals in which cancer has been diagnosed using the methods of this invention. Therapeutic compositions comprising FDNB-tagged cells may be used for therapy within about 24 hours of their preparation. However, TMCSA antigen compositions, such as affinity purified preparations, have a shelf life of greater than one year and may therefore be stored.

A further advantage of the present invention lies in the fact that in most cases of immunotherapy of cancer with tumor-derived materials, attenuated cancer cells or products obtained from such cells have been tested. According to the present invention, a "tumor-mimetic" material derived completely from normal, non-cancerous tissue is the source of a therapeutic composition.

Having now generally described the invention, the same will be more readily understood through reference to the following examples which are provided by way of illustration, and are not intended to be limiting of the present invention, unless specified.

EXAMPLE I

Preparation and Testing of TMCSA and anti-TMCSA Antibody

The TMCSA was produced as follows. Normal white blood cells (leucocytes), freed from red blood cells and other plasma constituents, were isolated from HIV-free-certified blood from normal, healthy blood group "O" volunteer donors. The leucocytes were incubated with FDNB in a concentration range of $10^2$ to $10^8$ molecules per cell.

A. Preparation of Antisera

Antisera specific against TMCSA were successfully raised in rabbits, horses and human subjects. The FDNB-modified cells were washed and injected into animals to raise antibodies specific for TMCSA. The antisera were subjected to the following treatments. (1) Complement was inactivated by heating the sera at 56° C. for 30 minutes. (2) Cross-reacting antibodies, including those arising from responses to species-specific antigens, tissue-specific antigens and HLA antigens, were removed by absorption. The antisera were exhaustively absorbed with pooled RBCs and WBCs from a large number of human donors until the antisera showed no reactivity with RBCs and WBCs from normal human subjects. (3) Immunoglobulins were enriched from the sera using fractional salt precipitations with saturated ammonium sulfate, using conventional procedures. The preparations were then subjected to isoelectric precipitation. Fractions were tested for reactivity against leukemic cells. Only those fractions showing reactivity against leukemic cells were collected for further testing and use.

B. Testing specificity of the antibodies

The specificity of purified immunoglobulin preparations for TMCSA was verified as follows: (i) Agglutination was demonstrated with all types of leukemic cells with the purified immunoglobulins (over 1000 samples tested). No agglutination was seen either with RBCs or WBCs isolated from over 1000 normal human subjects. (ii) Cytolytic activity against leukemic cells was demonstrated in the presence of complement or by complement fixation assays. (iii) KCl extracts were prepared using a variety of solid tumors obtained at biopsy or post-operatively. These extracts were used to coat sheep RBCs. The antibodies specific for TMCSA had high hemagglutinating titers with KCl extracts of all tumors tested. (iv) The anti-TMCSA antibodies gave clear precipitin lines in Ouchterlony immunodiffusion assays using membrane extracts from a variety of tumor cell types. No precipitin lines were seen with membrane extracts of RBCs and WBCs from normal healthy donors. In addition membrane extracts of liver, lung and skin tissue from post-mortem specimens from persons who had died in road accidents did not show the precipitin lines.

C. Isolation of TMCSA

Crude membrane preparations were made from DNFB-tagged cells by osmotic lysis. The material was centrifuged at 40,000×g and the pellet washed several times to remove soluble cytoplasmic material and nuclear material. The preparation was solubilized by incubating membranes with sodium dodecyl sulfate (SDS) at about 5.7 mg/3.6 mg protein for about 30 min at 37° C. The solubilized solution was centrifuged at 100,000×g for 1 hr to remove insoluble material. SDS was removed by prolonged dialysis against distilled water. The membrane protein-containing preparation was suspended in 0.1M $NaHCO_3$, pH 8.5.

The anti-TMCSA immunoglobulin preparation, as that described above, was coupled to CNBr-activated Sepharose beads using convention methods, by mixing and stirring overnight at 4° C. This material was subjected to extensive washing with PBS until the washings showed spectrophotometric absorptions of less than 0.02 absorption units at 280 nm. The extent of coupling was 90%. The antibody-Sepharose beads were stored at 4° C. in the presence of $NaN_3$ until use.

The affinity chromatography may be performed as follows. The solubilized membrane preparation from DNFB-tagged cells (25–50 mg) is loaded onto an antibody-Sepharose column (20 g) equilibrated with 0.1M bicarbonate. The flow is stopped for about 10–15 minutes to allow antigen-antibody binding to occur. Unabsorbed material is washed with 40 ml of 0.1M bicarbonate. The absorbed material is eluted with 0.1M acetic acid (pH 2.5). For example, about 6 fractions each of 4 ml, may be collected. The eluate is neutralized with 2N NaOH and dialyzed against PBS, pH 6.8.

Isolation of TMCSA from the membranes of chemically modified normal non-malignant cells was carried out as follows. The purified anti-TMCSA immunoglobulins were immobilized on Sepharose beads and used to affinity purify TMCSAs from membrane preparations of FDNB-treated leucocytes. Water soluble fractions of the membranous material from the chemically-modified normal cells was passed over the affinity column prepared with the purified antibodies.

Antigenicity of TMCSA preparations was tested by immunizing suitable animals with the affinity purified material and demonstrating the immunological reactivities against leukemic cells by agglutination and/or Ouchterlony immunodiffusion. Antigenicity of TMCSA is 300 times stronger than the antigenicity seen on leukemic cells, measured by relative activity of antisera against leukemic cells vs. FDNB-modified normal cells.

EXAMPLE II

Reactivity of TMCSA with Patient Lymphocytes

The antigens were used to test reactivity of lymphocytes from subjects having or being suspected of having cancer.

A. Leucocyte Migration Inhibition Assay

Ten ml of blood from each subject was collected in the presence of anticoagulant. Immediately upon collection, 5 ml of 4% dextran was added to every 10 ml sample. RBCs were allowed to settle for about 1 hr. The supernatant fluid, along with buffy coat, was aspirated and centrifuged for 2 minutes at 1500 rpm to separate the white blood cells from the plasma, anticoagulant, etc. Leucocytes were freed from contaminating RBCs by osmotic shock treatment with 0.83% ammonium chloride for one minute.

The separated leucocytes which form a button at the bottom of centrifuge tube were resuspended in MEM medium supplemented with antibiotics and 10% fetal calf serum (FCS). The cells were centrifuged again at 1500 rpm for 2 min. This process of alternate washing and centrifugation was repeated several times, preferably four times. Washed cells were resuspended in fresh MEM (+antibiotics and FCS) to a concentration of $10^8$ viable cells/ml. Viability of the cells was assessed by dye-exclusion. 75 µl of cell suspension was taken up in a capillary tube of approximately 0.5 mm inner diameter. One end of the tube was sealed with high vacuum silicon grease and plasticene.

Capillary tubes containing the cell suspension were centrifuged at 1500 rpm for 2 min to loosely pack the cells toward the sealed end of the tube. The capillary tubes were cut at the cell-medium interphase levels. Cut pieces containing cells were horizontally secured in migration chambers with an inner diameter 1.6 cm, depth of 2 mm, and capacity of 0.5 ml. The chambers were filled with MEM (alone in the case of controls) or MEM containing TMCSA (100 µg protein per chamber). Individual chambers were covered with cover glass and sealed with high vacuum silicon grease. The assembly was incubated at 37° C. for 18 hr, allowing the cells to migrate out of the capillary tube.

The extent of migration of cells in the control and experimental chambers was monitored by determining the area traversed by the migrating cells.

Sensitized lymphocytes from cancer patients recognized the TMCSA and responded by releasing cytokines which resulted in inhibition of migration of the leucocytes. Lymphocytes from normal subjects which are not sensitized to tumor antigens were unreactive with the TMCSA preparation.

B. Enzyme Immunoassay to Measure Cell Binding to TMCSA

An affinity purified TMCSA preparation was made as described above, by passing membrane preparations From FDNB-modified cells over an anti-TMCSA affinity column. The affinity purified TMCSA was conjugated to horseradish peroxidase using glutaraldehyde. The conjugate was prepared at a ratio of 1 mg TMCSA protein per 200 units of peroxidase enzyme.

Blood leucocytes were prepared as described in Section. A. above. To the washed leucocytes was added 5% freshly prepared hydrogen peroxide in 50% methanol to block endogenous peroxidase activity. The reaction was allowed to continue for 15 min. at 30° C. The cells were alternately washed with normal saline and centrifuged until the supernatant was free of peroxidase activity. The washed cells ($1 \times 10^7$) were treated with TMCSA-peroxidase conjugate at 30° C. for 15 min. The cells were then alternately washed with normal saline and centrifuged at 1500 rpm for 2 min until the supernatant washings were free of unreacted TMCSA-peroxidase. The washed cell button received peroxidase substrate (amino antipyrine benzoic acid) and color was allowed to develop for 15 min. The color was read at a wavelength of 495 nm.

Controls in this assay included TMCSA-peroxidase added to tube with no cells, and leucocytes from healthy individuals (not harboring latent or premalignant lesions). Such controls give readings of the order of 0.002 absorbance units. Sensitized lymphocytes from patients who had cancer of any histopathological type gave values which were significantly higher (at least two standard deviations); many were of about 0.200 absorbance units. Thus, sensitized lymphocytes have the capacity to bind the TMCSA. It is likely that B lymphocytes are the main cells detected in this assay.

The ability of TMCSA to identify a subject at risk of cancer was verified by using the screening method to two groups of individuals: The POSITIVE CONTROL GROUP consisted of patients having various types of tumors and included over 100 histopathologically-confirmed cancer cases. The NEGATIVE CONTROL GROUP consisted of over 100 patients visiting out-patient departments and having diseases other than cancer. All samples from the Positive Control Group showed the presence of cancer cells, whereas in the Negative Control Group, only 2 non-cancer patients showed any evidence of reactivity with the TMCSA.

A subset of these patients are listed in Table 1, below.

Thus, patients having the types of cancer indicated, in addition to leukemia, have now been shown to have lymphocytes which respond positively to TMCSA preparations.

Predictability of the above methods was confirmed by exploratory surgery and direct demonstrations of cancerous foci after an earlier diagnosis using the present method. An interesting example is a patient who tested positive in the above diagnostic assays, but was found to be negative for tumor by biopsy. A second round of exploratory surgery found that, indeed, there was tumor tissue present, indicating that the initial biopsy has missed the tumor site and contained only normal tissue.

Thus, patients having the types of cancer indicated, in addition to leukemia, have now been shown to have lymphocytes which respond positively to TMCSA preparations.

TABLE 1

Listing of Multiple Histologic Types of Tumors from Various Anatomic Locations which gave rise to Sensitized Lymphocytes Detected by LMI or Enzyme Immunosassays*

| Tumor/Location | Number of Cases | Histologic Diagnosis |
| --- | --- | --- |
| Alveolus | 5 | Squamous carcinoma |
| Larynx | 3 | Squamous carcinoma |
| Mandible | 2 | Squamous carcinoma |
| Cheek | 4 | Squamous carcinoma |
| Esophagus | 6 | Squamous carcinoma |
| Buccal mucosa | 1 | Squamous carcinoma |
| Breast | 26 | Invasive ductal cell carcinoma |
| Maxilla | 2 | Squamous carcinoma |
| Rectum | 5 | Squamous carcinoma |
| Stomach | 4 | Adenocarcinoma |
| Colon | 3 | Adenocarcinoma |
| Uterus | 2 | Sarcoma |
| Ovary | 3 | Adenocarcinoma |
| Cervix | 3 | Squamous carcinoma |
| Hodgkin's Lymphoma | 1 | Hodgkin's Lymphoma |
| Nasopharynx | 1 | Squamous carcinoma |
| Thyroid | 1 | Carcinoma |
| Melanoma | 1 | Melanoma |
| Endometrium | 2 | Adenocarcinoma |
| Tongue | 1 | Squamous carcinoma |
| Penis | 1 | Squamous carcinoma |
| Bladder | 1 | Carcinoma |
| Oral cavity | 2 | Squamous carcinoma |
| Hemangioma | 1 | Hemangioma |
| Bronchus | 1 | |
| Bone | 1 | |
| Liver | 1 | Hepatoma |

*All patients indicated were positive in both LMI and EIA.

Predictability of the above methods was confirmed by exploratory surgery and direct demonstrations of cancerous loci after an earlier diagnosis using the present method. An interesting example is a patient who tested positive in the above diagnostic assays, but was found to be negative for tumor by biopsy. A second round of exploratory surgery found that, indeed, there was tumor tissue present, indicating that the initial biopsy has missed the tumor site and contained only normal tissue.

Another example is of a false positive clinical diagnosis of cancer which was corrected following testing of the patient with the present methods. In this case, colostomy was advised to remove intestinal blockages presumed to be caused by malignant growths. However, LMI and EIA measuring reactivity to TMCSA yielded negative results. Interpreted in light of the present disclosure, it was predicted that this patient did not have a malignancy. Indeed, subsequent surgical exploration confirmed that the intestinal blockage was not neoplastic in nature and the colostomy was avoided.

Thus, assay results not only correlated completely with later obtained histologic confirmation of cancer but were able to diagnose the presence (or absence) of cancer in cases where traditional diagnostic means indicated otherwise.

In all known cases of cancer, there was never an instance where the patients leucocytes did not react positively in the LMI test or EIA. To date, over 300 patients have been tested with various type of cancer, including solid tumors. Each manifested (a) cell-mediated immunity to FDNB-modified cells or TMCSA by lymphocyte migration inhibition and (b) binding of TMCSA-enzyme conjugates to their lymphocytes.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A method for detecting the presence of a non-leukemia form of cancer in a subject having lymphocytes sensitized to a tumor antigen, which method comprises
    (a) obtaining a sample of blood from said subject; and
    (b) assaying the reactivity of leucocytes of said sample in vitro with a tumor-mimetic cell surface antigen (TMCSA) which TMCSA is produced by treating cells with a chemical agent which is a nucleophilic reagent with one leaving group and between one and three electron-withdrawing groups having one or more of the following properties when the cells are treated at a temperature and pH which are non-toxic:
        (i) converts hydrophilic sites to hydrophobic sites on the surface of said cells;
        (ii) causes a gain or loss of HLA antigens on the surface of said cells; or
        (iii) causes a change to the surface of leukocytes similar to changes induced by fluorodinitrobenzene under substantially similar conditions
    wherein said TMCSA is in the form of either:
        (A) intact normal human cells which have been chemically treated with said chemical agent such that TMCSA is present on their surface;
        (B) solubilized membranes of said treated cells of (A); or
        (C) affinity purified TMCSA produced from said solubilized membranes of (B) using a TMCSA-specific antibody,
    wherein the detection of reactivity with said TMCSA indicates the presence of said non-leukemia form of cancer in said subject.

2. The method of claim 1, wherein said treated normal human cells are leucocytes or skin cells.

3. The method of claim 1, wherein said chemical agent is a halobenzene derivative or a benzene sulfonate derivative.

4. The method of claim 1, wherein said assaying measures the binding of said sample leucocytes to said TMCSA.

5. The method of claim 4 wherein said TMCSA is said affinity purified TMCSA.

6. The method of claim 4 wherein said binding is measured in an enzyme immunoassay using enzyme-labeled TMCSA.

7. The method of claim 6 wherein said TMCSA is said affinity-purified TMCSA and said enzyme label is horseradish peroxidase.

8. The method of claim 1, wherein said assaying measures the stimulation or activation of leucocytes in said sample by said TMCSA.

9. The method of claim 8, wherein said stimulation is measured as the proliferation of lymphocytes among said sample leucocytes.

10. The method of claim 8, wherein said stimulation is measured as the inhibition of migration of said sample leucocytes stimulated by said TMCSA.

11. The method of claim 8, wherein said stimulation is measured as the production of a cytokine by said sample leucocytes.

12. The method of claim 1, wherein said cancer is selected from the group consisting of an adenocarcinoma, a squamous cell carcinoma, a breast duct cell carcinoma, a sarcoma, a melanoma, a hemangioma, a hepatoma and a lymphoma.

13. A method for detecting the presence of lymphocytes in a subject which are sensitized to a tumor antigen and are reactive with TMCSA, which method comprises
    (a) obtaining a sample of blood from said subject;
    (b) assaying in vitro
        (i) reactivity other than antibody secretion, or
        (ii) binding
            of leucocytes of said sample with a TMCSA produced by treating cells with a chemical agent which is a nucleophilic reagent with one leaving group and between one and three electron-withdrawing groups; having one or more of the following properties when the cells are treated at a temperature and pH which are non-toxic:
            (A) converts hydrophilic sites to hydrophobic sites on the surface of said cells;
            (B) causes a gain or loss of HLA on the surface of said cells; or
            (C) causes a change to the surface of leukocytes similar to changes induced by fluorodinitrobenzene under substantially similar conditions
            which TMCSA is in the form of either:
                (1) normal human cells which have been chemically treated with said chemical agent such that TMCSA is present on their surface;
                (2) solubilized membranes of said treated cells of (1); or
                (3) affinity purified TMCSA produced from said solubilized membranes of (2) using a TMCSA-specific antibody,
        wherein detection of reactivity or binding of said leucocytes with said TMCSA indicates the presence of said sensitized lymphocytes.

14. The method of claim 13, wherein said chemical agent is a halobenzene derivative or a benzene sulfonate derivative.

15. A method for monitoring therapy in a non-leukemia cancer patient to detect a therapeutic effect, which method comprises:
    (a) subjecting said patient to a cancer therapy;
    (b) obtaining a sample of blood from said patient at two or more time points during said therapy, after said therapy, or both;
    (c) assaying in vitro
        (i) reactivity other than antibody secretion, or
        (ii) binding
            of leucocytes of said sample with a TMCSA produced by treating cells with a chemical agent which is a nucleophilic reagent with one leaving group and between one and three electron-withdrawing groups; having one or more of the following properties when the cells are treated at a temperature and pH which are non-toxic:
            (A) converts hydrophilic sites to hydrophobic sites on the surface of said cells;
            (B) causes a gain or loss of HLA on the surface of said cells; or
            (C) causes a change to the surface of leukocytes similar to changes induced by fluorodinitrobenzene under substantially similar conditions
            which TMCSA is in the form of either:
                (1) normal human cells which have been chemically treated with said chemical agent such that TMCSA is present on their surface;
                (2) solubilized membranes of said treated cells of (1); or
                (3) affinity purified TMCSA produced from said solubilized membranes of (2) using a TMCSA-specific antibody,
        wherein a decrease in said reactivity or binding from one time point before, during or after therapy to a subsequent time point during or after therapy is an indication of a therapeutic effect.

16. The method of claim 15, wherein said chemical agent is a halobenzene derivative or a benzene sulfonate derivative.

17. A kit for use in an enzyme assay to detect the presence of lymphocytes sensitized to a tumor antigen, said kit being compartmentalized to receive in close confinement therein one or more containers, said kit comprising a first container containing a TMCSA preparation conjugated to an enzyme, which TMCSA comprises
    (a) normal human cells which have been chemically treated with chemical agent which is a nucleophilic reagent with one leaving group and between one and three electron-withdrawing groups having one or more of the following properties when the cells are treated at a temperature and pH which are non-toxic:
        (i) converts hydrophilic sites to hydrophobic sites on the surface of said cells;
        (ii) causes a gain or loss of HLA antigens on the surface of said cells; or
        (iii) causes a change to the surface of leukocytes similar to changes induced by fluorodinitrobenzene under substantially similar conditions
    (b) solubilized membranes of said treated cells of (a); or
    (c) affinity purified TMCSA produced from said solubilized membranes of (b) using an TMCSA-specific antibody,
    which preparation binds detectably to lymphocytes sensitized to a tumor antigen.

18. A kit according to claim 17, further comprising a container containing a chromogenic substrate for said enzyme.

19. A kit according to claim 17, further comprising a plurality of additional containers containing reagents needed for said assay.

20. The kit of claim 17, wherein said chemical agent is a halobenzene derivative or a benzene sulfonate derivative.

* * * * *